United States Patent [19]

Shumanov et al.

[11] Patent Number: 5,225,338

[45] Date of Patent: Jul. 6, 1993

[54] MICROBIAL PREPARATION OF 13β-13-DEOXY-22,23-DIHYDRO AVERMECTIN-B1A/B1B AGLYCONE

[75] Inventors: Kalinka Shumanov, Bradley Beach; Raymond F. White, Englishtown, both of N.J.

[73] Assignee: Merck & Co., Inc., Rahway, N.J.

[21] Appl. No.: 587,290

[22] Filed: Sep. 24, 1990

[51] Int. Cl.$^5$ .................. C12P 17/18; C12P 1/04; C12N 1/20

[52] U.S. Cl. .................. 435/119; 435/170; 435/820; 435/252.1; 435/253.5

[58] Field of Search ........... 435/119, 170, 820, 252.1, 435/253.5

[56] References Cited

U.S. PATENT DOCUMENTS 4,587,247  5/1986  Linn et al. .................. 514/222

4,666,937  5/1987  Goegelman et al. .................. 514/450

OTHER PUBLICATIONS

JACS 75 p. 5764 (1953).

*Primary Examiner*—Irene Marx
*Attorney, Agent, or Firm*—Sylvia A. Ayler; Mark Daniel; Joseph F. DiPrima

[57] ABSTRACT

The known compound, 13β-13-deoxy-22,23-dihydroavermectin -B1a/B1b Aglycone is prepared microbiologically from cultures of the novel microorganisms (MA-6762, ATCC 55069, MA-6763 ATCC 55070) or the known microorganism *Streptomyces lavendulae* MA-6555 (ATCC 14159 or ATCC 55330). The compound is prepared by the biotransformation of 13-deoxy-22,23-dihydro avermectin B1a/B1b aglycone which oxidizes the 13-position and epimerizes the 13-position hydroxy group.

12 Claims, No Drawings

MICROBIAL PREPARATION OF 13β-13-DEOXY-22,23-DIHYDRO AVERMECTIN-B1A/B1B AGLYCONE

BACKGROUND OF THE INVENTION

The compound prepared by the process of this invention is a known compound disclosed in U.S. Pat. No. 4,587,247. The compound can be prepared through an ardous chemical epimerization, and has also been prepared microbiologically as described in U.S. Pat. No. 4,666,937. The instant process offers a novel preparation of the 13-β compound directly from the natural product 13-α- compound using any one of three microorganisms, two of which are novel.

SUMMARY OF THE INVENTION

The instant invention is concerned with a novel process for the preparation of the instant compound, 13-β-22,23-dihydro avermectin B1a/B1b agylcone, which is useful as an anthelmintic and antiparastic agent and also useful as an intermediate for the preparation of other anthelmintic agents. Thus, it is an object of this invention to disclose the preparation of the above compound by the biotransformation fermentation of the starting material 13-deoxy-22,23-dihydro avermectin B1a/B1b aglycone. A further object is to describe the methods used to isolate the desired product from the fermentation broth. A still further object is to describe the two novel microorganisms (MA-6762, ATCC 55069) and (MA-6763, ATCC 55070) along with the known microorganism Streptomyces lavendulae MA-6555, ATCC 14159 or ATTC 55330 which are capable of performing the biotransformation reaction. Further objects will become apparent from a reading of the following description.

DESCRIPTION OF THE INVENTION

The first aspect of the instant invention is a process for the preparation of the compound having the structure:

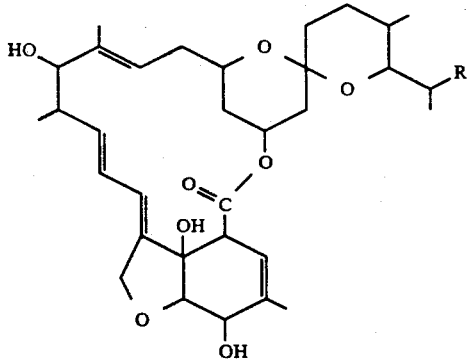

where R is ethyl (a compounds) or methyl (b compounds).

The compound is named as 13-β-22,23-dihydro avermectin B1a/B1b agylcone. The compound is produced in a microbial transformation reaction from 13-deoxy-22,23-dihydro avermectin B1a/B1b aglycone that is, the analogous compound missing the 13-hydroxy group. In addition, the product is epimerized with reversed stereochemistry at the 13-position, when compared with the avermectin natural products. The instant process as thus a microbial oxidation and epimerization at the 13-position.

The microbial bioconversion reaction is carried out using any one of three microorganisms. Two of these microorganisms are novel and these microorganisms form the second aspect of the instant invention. The third microorganism is known and publicly available from the American Type Culture Collection.

In accordance with this invention, a novel process is described in which the above compound is prepared by growing under controlled conditions a strain of microorganism Streptomyces griseus and including in the fermentation broth a substrate which is the 13-deoxy-22,23-dihydro avermectin B1a/B1b aglycone compound. These microorganisms are identified in the Merck Culture Collection as MA-6762 and MA-6763 and are publicly available from the American Type Culture Collection at 12301 Parklawn Drive, Rockville, Md. 20852 under the accession numbers ATCC 55069 and 55070 respectively.

The morphological and cultural characteristics of MA-6762, ATCC 55069 and MA-6763, ATCC 55070 are as follows.

The following is a general description of strains MA6762 and MA6763. Observations of growth, general cultural characteristics and carbon source utilization were made in accordance with the methods of Shirling and Gottleib (Internat. J. System. Bacteriol. 16: 313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

Deposits—MA-6762 was deposited as ATCC 55069 and MA-6763 was deposited as ATCC 55070 on Jul. 11, 1990, under the terms of the Budapest Treaty for the International Recognition of the Deposit of Microorganisms for the Purposes of Patent Procedure. MA-6555, originally deposited as ATCC 14159 is now, as of Jun. 16, 1992, deposited under the Budapest Treaty as ATCC 55330.

Analysis of Cell Wall Composition—MA-6762 Peptidoglycan contains L-diaminopimelic acid, whole cell sugar analysis reveals glucose and traces of xylose. MA-6763 Peptidoglycan contains L-diaminopimelic acid, whole cell sugar analysis reveals glucose.

General growth characteristics—MA-6762 and MA-6763 Both strains growth well on Yeast Malt Extract, Glycerol Asparagine, Inorganic Salts-Starch, Oatmeal, and Trypticase Soy agars. Growth occurs at 27° and 37° C. Both cultures also grow well in liquid media such as Yeast Dextrose broth.

Colony morphology (on Yeast Malt Extract Agar @ 21d) MA-6762—Substrate mycelium is medium olive brown (95 m.O1Br) and colonies are opaque, raised, filamentous and soft to rubbery. The colony surface is matte to rough in appearance. Aerial mycelia appear after 4 days incubation and are yellow white in color (92 yWhite). Spore mass, when present, is deep yellow brown (75 deep yBr). MA-6763—Substrate mycelium is medium brownish black (65 brBlack) and colonies are opaque, raised, filamentous and rubbery. The colony surface is rough. Aerial mycelia appear after 4 days incubation and are yellow white in color (92 yWhite). Spore mass, when present, is yellow white (92 yWhite).

Micromorphology—MA-6762 Aerial mycelium (0.76 μm dia.) arises from a substrate mycelium and is branched and flexous. In mature cultures, aerial mycelia terminate in chains of spores that are borne in straight chains. MA-6763 Aerial mycelium (0.76 μm dia.) radiate from the substrate mycelium and is straight. In mature cultures, aerial mycelia terminate in chains of spores that are borne in flexous chains.

Miscellaneous physiological reactions—MA-6762 Culture does not produce melanoid pigments in tryptone yeast extract broth, starch is hydrolyzed, $H_2S$ is produced on Peptone-Iron agar. A diffusible yellow pigment is produced on Pridham-Gottlieb Basal Medium supplemented with 1% cellobiose or D-mannose and a reddish brown diffusible pigment on Pridham-Gottlieb Basal Medium supplemented with 1% D-fructose, α-D-glucose, β-D-lactose, D-maltose, D-mannitol, L-rhamnose. Carbon source utilization pattern is as follows: moderate utilization of cellobiose, D-fructose, α-D-lactose, β-D-lactose, D-maltose, D-mannitol, D-mannose, L-rhamnose, D-xylose; poor utilization of inositol, sucrose; no utilization of D-arabinose, L-arabinose, D-raffinose, L-xylose. MA-6763—Culture produces melanoid pigments in tryptone yeast extract broth, yeast extract agar, and peptone yeast extract iron agar in 2-7 d. Starch is weakly hydrolyzed, $H_2S$ is produced on Peptone-Iron agar. A diffusible purple pigment is produced on Pridham-Gottlieb Basal Medium supplemented with 1% cellobiose, D-fructose, α-D-glucose, β-D-lactose, D-maltose, D-mannitol, D-mannose, L-rhamnose. Carbon source utilization pattern is as follows: moderate utilization of cellobiose, D-fructose, α-D-lactose, β-D-lactose, D-maltose, D-mannitol, D-mannose, L-rhamnose, D-xylose; no utilization of D-arabinose, L-arabinose, inositol, D-raffinose, sucrose, L-xylose.

The carbohydrate utilization patterns for MA-6762 and MA-6763 are summarized in Table 1 and the cultural characteristics of MA-6762 and MA-6763 are summarized in Table 2.

Diagnosis—The chemotaxonomic and morphological characteristics of these strains compare favorably with the published description of members of the genus Streptomyces. These strains bear a strong similarity to one another, and, differ mainly with respect to the production of melanin on Peptone-Iron agar and a diffusible purple pigment on Yeast Malt Extract, Glucose Asparagine and Inorganic Salts-Starch agars. A review of the validly published descriptions of Streptomyces species shows a strong similarity between these strains and those commonly placed into the *Streptomyces griseus* complex. As such, both MA-6762 and MA-6763 are tentatively identified as strains of *Streptomyces griseus*.

TABLE 1

Carbohydrate utilization pattern of strains MA-6762 and MA-6763 at 21 days

| Carbon source | Utilization by MA-6762 | Utilization by MA-6763 |
|---|---|---|
| D-arabinose | 0 | 0 |
| L-arabinose | 0 | 0 |
| cellobiose | 2 | 2 |
| D-fructose | 2 | 2 |
| inositol | 1 | 0 |
| α-D-lactose | 2 | 2 |
| β-D-lactose | 2 | 2 |
| D-maltose | 2 | 2 |
| D-mannitol | 2 | 2 |
| D-mannose | 2 | 2 |
| D-raffinose | 0 | 0 |
| L-rhamnose | 2 | 2 |
| sucrose | 1 | 0 |
| D-xylose | 2 | 2 |
| L-xylose | 0 | 0 |
| a-D-glucose (control) | 2 | 2 |

3 = good utilization, 2 = moderate utilization, 1 = poor utilization, 0 = no utilization.

TABLE 2

Cultural characteristics of MA-6762 and MA-6763 at 21 days

| | Amount of Growth | | Aerial Mycelium | | Soluble Pigments | | Substrate Mycelium | |
|---|---|---|---|---|---|---|---|---|
| Medium | MA-6762 | MA-6763 | MA-6762 | MA-6763 | MA-6762 | MA-6763 | MA-6762 | MA-6763 |
| Yeast Extract Malt Extract | good | good | Yellow white (92, yWhite). Sporophores flexuous, clustered. | Yellow white (92, yWhite). Sporophores flexuous, clustered. | none noted | Purple | Deep yellow brown (75 deep yBr) with dark yellow brown edges (78 d. yBr). | Brown black (65 Br.Bl). |
| Glucose Asparagine | good | good | Yellow white (92, yWhite). Sporophores flexuous, clustered. | Yellow white (92, yWhite). Sporophores flexuous, clustered. | none noted | Purple | Pale orange, yellow (73 p. OY). | Dark gray purple (47 d.gy.rBr). |
| Inorganic Salts Starch | good | good | Yellow white (92, yWhite). Edge of colonies grayish-green yellow (105 gy. gY) Sporophores flexuous, clustered. | Yellow white (92, yWhite). Sporophores flexuous, clustered. | none noted | Purple | Gray yellow (90 g.Y). | Dark olive brown (96 d. OlBr). |
| Oatmeal | good | good | Yellow white (92, yWhite). Sporophores flexuous, clustered. | Yellow white (92, yWhite). Sporophores flexuous, clustered. | none noted | none noted | Gray yellow (90 g.Y) | Gray yellow (90 g.Y) |
| Sigma Water | sparse | sparse | Yellow white (92, yWhite). Sporophores flexuous, clustered. | No aerial mycelia. | none noted | none noted | Yellow white (92 yWhite) | Yellow white (92 yWhite) |
| Czapek | fair | fair | Yellow white (92, yWhite). Sporophores | White (263 White) Sporophores flexuous, | none noted | none noted | Yellow white (92 yWhite) | Yellow white (92 yWhite) |

TABLE 2-continued

| | Cultural characteristics of MA-6762 and MA-6763 at 21 days | | | | | | | |
|---|---|---|---|---|---|---|---|---|
| | Amount of Growth | | Aerial Mycelium | | Soluble Pigments | | Substrate Mycelium | |
| Medium | MA-6762 | MA-6763 | MA-6762 | MA-6763 | MA-6762 | MA-6763 | MA-6762 | MA-6763 |
| Peptone Iron | good | good | flexuous, clustered. | clustered. | melanin negative, H2S positive | melanin positive H2S positive | | |

In addition, the novel process can be carried out by growing under controlled conditions a strain of the known microorganism indentified as *Streptomyces lavendulae* and including in the fermentation broth the above substrate. This microorganism is identified in the Merck Culture Collection as MA-6555 and is publicly available from the American Type Culture Collection at 12301 Parklawn Drive, Rockville, Md. 20852 under the accession number ATCC 14159. A description of the culture *Streptomyces lavendulae* MA-6555, ATCC 14159 or ATCC 55330 is found in *Journal of the American Chemical Society*, 75, 5764 (1953).

The publicly available deposit of *Streptomyces lavendulae*, ATCC 14159, has been supplemented to ensure that the culture is available for the full term of the patent.

The instant compound is produced during the aerobic fermentation of suitable aqueous nutrient media under conditions described hereinafter, with a producing strain of MA-6762, ATCC 55069 or MA-6763, ATCC 55070, or a producing strain of *Streptomyces laveudulae* MA-6555, ATCC 14159 or ATCC 55330. Aqueous media such as those used for the production of many antibiotic substances are suitable for use in the process for the production of the oxidized, epimeric macrocyclic compound.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by MA-6762, ATCC 55069, MA-6765, ATCC 55070, or *Streptomyces lavendulae* MA-6555, ATCC 14159 or ATCC 55330 in the production of the instant compound. The various sources of nitrogen can be used alone or in combination in amounts ranging from 1 to 5 g/l in the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of MA-6762, ATCC 55069, MA-6763, ATCC 55070, or *Streptomyces lavendulae*, MA-6555, ATCC 14159 or ATCC 55330:

| Composition of Media | |
|---|---|
| Medium 1 | |
| Dextrose | 20 g. |
| Peptone | 5 g. |
| Meat Extract | 5 g. |
| Primary Yeast | 3 g. |
| NaCl | 5 g. |
| CaCO$_3$ (after pH adjustment) | 3 g. |
| Distilled Water | 1000 ml. |
| pH 7.0 | |
| Medium 2 | |
| Tomato Paste | 20 g. |
| Modified Starch (CPC) | 20 g. |
| Primary Yeast | 10 g. |
| CoCl$_2$6H$_2$O | 0.005 g. |
| Distilled Water | 1000 ml. |
| pH 7.2–7.4 | |
| Medium 3 (Slant Medium) | |
| Dextrose | 10.0 g. |
| Bacto Asparagine | 0.5 g. |
| K$_2$HPO$_4$ | 0.5 g. |
| Bacto Agar | 15.0 g. |
| Distilled Water | 1000 ml. |
| pH 7.0 | |
| Medium 4 (Seed Medium) | |
| Soluble Starch | 10.0 g. |
| Ardamine pH | 5.0 g. |
| NZ Amine E | 5.0 g. |
| Beef Extract | 3.0 g. |
| MgSO$_4$7H$_2$O | 0.5 g. |
| Cerelose | 1.0 g. |
| Na$_2$HPO$_4$ | 0.190 g. |
| KH$_2$PO$_4$ | 0.182 g. |
| CaCO$_3$ | 0.5 g. |
| Distilled Water | 1000 ml. |
| pH 7.0–7.2 | |
| Medium 5 | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |
| pH 6.8 | 1000 ml. |
| Trace Element Mix | 1000 ml. |
| FeSO$_4$.7H$_2$O | 1000 mg. |

| Composition of Media | |
| --- | --- |
| MnSO$_4$.4H$_2$O | 1000 mg. |
| CuCl$_2$.2H$_2$O | 25.0 g. |
| CaCl$_2$ | 100.0 mg. |
| H$_2$BO$_3$ | 56.0 mg. |
| (NH$_4$)$_2$MoO$_4$.4H$_2$O | 10.0 mg. |
| ZnSO$_4$.7H$_2$O | 200.0 mg. |
| Distilled Water | 1000 ml. |
| pH | |
| Medium 6 | |
| CPC Industrial Starch Modified (Available from CPC Corp.) | 40.0 g. |
| Distiller's Solubles | 7.0 g. |
| Autolyzed Yeast (Ardamine pH available from Yeast Products Inc.) | 5.0 g. |
| CoCl$_2$.6H$_2$O | 50.0 mg. |
| Distilled Water | 1000 ml. |
| pH 7.3 | |

The fermentation employing *Streptomyces griseus* MA-6762, ATCC 55069 or MA-6763, ATCC 55070, or *Streptomyces lavendulae* MA-6555, ATCC 14159 or ATCC 55330, can be conducted at temperatures ranging from about 20° C. to about 40° C. For optimum results, it is most convenient to conduct these fermentations at a temperature in the range of from about 24° C. to about 30° C. Temperatures of about 27°-28° C. are most preferred. The pH of the nutrient medium suitable for producing the instant compounds can vary from about 5.0 to 8.5 with a preferred range of from about 6.0 to 7.5.

The substrate compound is added to the fermentation of *Streptomyces griseus* MA-6762, ATCC 55069, MA-6763, ATCC 55070, or *Streptomyces lavendulae* MA-6555, ATCC 14159 or ATCC 55330 in quantities of from 0.01 to 1.0 mg per milliliter of fermentation medium. It is preferred to use from 0.05 to 0.5 mg per milliliter. The substrate compound may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the substrate compound be added to the fermentation before 50% of the cycle is completed, preferably before 25% of the cycle is completed.

Small scale fermentations are conveniently carried out by placing suitable quantities of nutrient medium in a flask employing known sterile techniques, inoculating the flask with either spores or vegetative cellular growth of *Streptomyces griseus* MA-6762, ATCC 55069, MA-6763, ATCC 55070 or *Streptomyces lavendulae* MA-6555, ATCC 14159 or ATCC 55330, loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces griseus* MA-6762, ATCC 55069, MA-6763, ATCC 55070, or *Streptomyces lavendulae* MA-6555, ATCC 14159 or ATCC 55330. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (LPM) of air.

The separation of the epimerized compound from the whole fermentation broth and the recovery of said compound is carried out by solvent extraction and application of chromatographic fractionations with various chromatographic techniques and solvent systems.

The instant compound has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as others known to those skilled in the art, will afford purified compositions containing the instant compounds. The presence of the desired compounds is determined by analyzing the various chromatographic fractions for biological activity of physico-chemical characteristics. The structures of the instant compounds have been determined by detailed analysis of the various spectral characteristics of the compounds, in particular their nuclear magnetic resonance, mass, ultraviolet and infrared spectra.

The oxidized and epimerized compound of this invention has significant parasiticidal activity as an anthelmintic, insecticide and acaricide, in human and animal health and in agriculture. In addition the 13-oxidized epimeric compound is useful as a starting material to prepare 13-$\beta$-substituted-13-deoxy avermectin compounds. Procedures for substitution at the 13-position of avermectin compounds are well known to those skilled in the art.

The following examples are provided in order that the instant invention may be more fully understood. The examples are not to be construed as limitative of the invention.

EXAMPLE 1

Transformation

An L-Tube of a selected culture is aseptically transferred to 30 ml of medium A in a 250 ml baffled Erlenmeyer flask. The seed flask is incubated on a rotary shaker (220 rpm) at 27° C. until the seed is developed. One ml of this seed is used to inoculate 10 ml of medium B containing 0.05 mg/ml of 13-deoxy-22,23-dihydro avermectin B1a/B1b agylcone.

| MEDIUM A | | MEDIUM B | |
|---|---|---|---|
| Dextrose | 1.0 g/l | Glucose | 10.0 g/l |
| Dextrin | 10.0 | Hycase SF | 2.0 |
| Beef Extract | 3.0 | Beef Extract | 1.0 |
| Ardamine pH | 5.0 | Corn Steep Liquor | 3.0 |
| NZ Amine Type E | 5.0 | Adj. pH 7.0 | |
| $MgSO_4.7H_2O$ | 0.05 | | |
| $K_2HPO_4$ | 0.3 | | |
| Adj. pH 7.1 | | | |
| Add $CaCO_3$ | 0.5 | | |

The tubes are incubated at 27° C. on a rotary shaker (220 rpm) for 7 days and the whole broth extracted with an equal volume of methylene chloride. The extracts are taken to dryness and the residue is dissolved in a known volume of methanol. Assay is by High Performance Liquid Chromatography (HPLC).

EXAMPLE 2

Assay

The HPLC analysis was performed on an analytical Dupont Sorbax ODS 4.6 mm×25 cm column eluted at 1 ml/min with methanol: water (80:20) at 60° C. The column was monitored at 243 nm. ultraviolet light for the presence of the avermectin product.

EXAMPLE 3

Production

A frozen vial (2 ml) of culture *Streptomyces griseus* MA-6762, ATCC 55069, MA-6763, ATCC 55070 or *Streptomyces lavendulae* MA-6555, ATCC 14159 was used to inoculate a 250 ml baffled Erlenmeyer flask containing 50 ml of medium A. The seed flask was incubated on a rotary shaker (220 rpm) at 27° C. for 24 hours. Five ml of the developed seed was used to inoculate a 250 ml Erlenmeyer flask containing 50 ml of transformation medium B. 13-deoxy-22,23-dihydro avermectin B1a/B1b aglyone dissolved in methanol was added to the transformation at 0 hour to a final concentration of 0.05 mg/ml. The transformation flasks (5) were incubated for 5 days at 27° C. and extracted as described in Example 4.

EXAMPLE 4

Isolation and Purification

The pooled whole broth (250 ml) of each culture was centrifuged and the clarified broth was extracted three times with methylene chloride (3×100 ml). The cell mass was extracted three times with acetone (3×100 ml). The extracts were combined and taken to dryness under vacumn, the oily residue was dissolved in methanol and subjected to HPLC. HPLC was carried out on Whatman Partisil 10 ODS-3, 9.4 mm×25 cm at 60° C. and monitored at 243 nm ultraviolet light. The column was developed at 3 ml/min with methanol: water (80:20) for 20 minutes. The compound was collected during repeated injections of the above extract. The fractions at 7.6 minutes were pooled and solvents evaporated to dryness.

EXAMPLE 5

Characterization

The products obtained from the above fermentation were characterized by nuclear magnetic resonance as 13-β-22,23-dihydro avermectin B1a/B1b aglycone and by comparison with an authentic sample.

What is claimed is:

1. A process for the preparation of 13-β-22,23-dihydro avermectin B1a/B1b aglycone which comprises fermenting in an aqueous nutrient medium with assimilable sources of carbon, nitrogen and inorganic salts, a culture of *Streptomyces griseus* MA-6762, MA-6763- selected from the group consisting of *Streptomyces griseus* MA-6762 ATCC 55069, *Streptomyces griseus* MA-6763 ATCC 55070, *Streptomyces lavendulae* MA-6555 ATCC 14159 and *Streptomyces lavendulae* MA-6555 ATCC 55330 and the added compound 13-deoxy-22,23-dihydro avermectin B1a/B1b aglycone in about 0.05 mg per milliliter of the fermentation medium and recovering 13-β-22,23-dihydro avermectin Bla/Blb aglycone and the added compound 13-deoxy-22,23-dihydro avermectin B1a/B1b and recovering the desired compound.

2. The process of claim 1 wherein the microorganism is *Streptomyces griseus* MA-6762 ATCC 55069.

3. The process of claim 1 wherein the microorganism is *Streptomyces griseus* MA-6763 ATCC 55070.

4. The process of claim 1 wherein the microorganism is *Streptomyces lavendulae* MA-6555 ATCC 14159 or *Streptomyces lavendulae* MA-6555 ATCC 55330.

5. The process of claim 1 wherein the source of carbon is present in the form of carbohydrate.

6. The process of claim 5 wherein the carbohydrate is present to the extent from 1 to 10 g per liter of the fermentation medium.

7. The process of claim 1 wherein the source of nitrogen is present at from 5 to 10 g per liter of the fermentation medium.

8. The process of claim 1 wherein the fermentation is carried out at from 20° to 40° C. and a pH from 5.0 to 8.5.

9. The process of claim 8 wherein the fermentation is carried out at from 24° to 30° C. and a pH of from 6.0 to 7.5.

10. The process of claim 9 wherein the fermentation is carried out at form 27° to 28° C.

11. The process of claim 1 wherein the added compound is added to the fermentation broth before 50% of the fermentation cycle is completed.

12. The process of claim 11 wherein the added compound is added to the fermentation broth before 25% of the fermentation cycle is completed.

* * * * *